(12) United States Patent
Kendirgi et al.

(10) Patent No.: US 10,760,101 B2
(45) Date of Patent: Sep. 1, 2020

(54) PROCESS AND MEDIUM FOR REDUCING SELENIUM LEVELS IN BIOMASS FROM FERMENTATION OF CO-CONTAINING GASEOUS SUBSTRATES

(71) Applicant: INEOS BIO SA, Rolle (CH)

(72) Inventors: Frédéric Kendirgi, Fayetteville, AR (US); Ryan H. Senaratne, Fayetteville, AR (US); Syrona R. Scott, Fayetteville, AR (US)

( * ) Notice: Subject to any disclaimer, the term of this patent is extended or adjusted under 35 U.S.C. 154(b) by 995 days.

(21) Appl. No.: 14/331,326

(22) Filed: Jul. 15, 2014

(65) Prior Publication Data
US 2015/0024449 A1  Jan. 22, 2015

Related U.S. Application Data

(60) Provisional application No. 61/857,044, filed on Jul. 22, 2013.

(51) Int. Cl.
*C12P 7/06* (2006.01)

(52) U.S. Cl.
CPC ............... *C12P 7/065* (2013.01); *C12P 7/06* (2013.01); *Y02E 50/17* (2013.01)

(58) Field of Classification Search
None
See application file for complete search history.

(56) References Cited

FOREIGN PATENT DOCUMENTS

WO  2013176947  11/2013

OTHER PUBLICATIONS

Saxena et al: "Effect of trace metals on ethanol production from synthesis gas by the ethanologenic acetogen, Clostridium ragsdalei", Journal of Industrial Microbiology and Biotechnology, vol. 38, 2011, pp. 513-521, XP055086240.
Guo et al: "Medium optimization for ethanol production with Clostridium autoethanogenum with carbon monoxide as sole carbon source", Bioresource Technology, vol. 101, 2010, pp. 8784-8789, XP027181715.
International Searching Authority, International Search Report and Written Opinion issued in PCT/US2014/047200, dated Oct. 22, 2014, 14 pages.

*Primary Examiner* — Robert J Yamasaki
*Assistant Examiner* — Charles Zoltan Constantine
(74) *Attorney, Agent, or Firm* — James P. Kreuger (57) ABSTRACT

A process for fermenting syngas and a fermentation medium provides high ethanol productivity while removing medium components that were previously thought to be essential. The process is effective for providing a specific STY of at least about 1 gram of ethanol/(L·day·gram cells) and for providing a selenium content in cell biomass exiting the fermentation of about 1 ppm or less.

2 Claims, 3 Drawing Sheets

PROCESS AND MEDIUM FOR REDUCING SELENIUM LEVELS IN BIOMASS FROM FERMENTATION OF CO-CONTAINING GASEOUS SUBSTRATES

This application claims the benefit of U.S. Provisional Application No. 61/857,044, filed Jul. 22, 2013, which is incorporated in its entirety herein by reference.

Processes and media are provided for reducing selenium levels in biomass exiting a fermentation of CO-containing gaseous substrates. More specifically, processes and media are provided that are effective for reducing selenium levels in cell biomass exiting the fermentation while maintaining a high level of ethanol productivity.

BACKGROUND

Fermentations take place in defined liquid media. These media will typically include various macro- and micro-nutrient sources that are important in improving fermentation performance. Media used in connection with less common substrates, such as gaseous substrates, require well defined media to optimize performance. Anaerobic fermentations also require well defined media.

Anaerobic microorganisms can produce ethanol from carbon monoxide (CO) through fermentation of gaseous substrates. Fermentations using anaerobic microorganisms from the genus *Clostridium* produce ethanol and other useful products. For example, U.S. Pat. No. 5,173,429 describes *Clostridium ljungdahlii* ATCC No. 49587, an anaerobic microorganism that produces ethanol and acetate from synthesis gas. U.S. Pat. No. 5,807,722 describes a method and apparatus for converting waste gases into organic acids and alcohols using *Clostridium ljungdahlii* ATCC No. 55380. U.S. Pat. No. 6,136,577 describes a method and apparatus for converting waste gases into ethanol using *Clostridium ljungdahlii* ATCC No. 55988 and 55989.

U.S. Pat. No. 7,285,402 describes media known for use in anaerobic fermentation of gaseous substrates to produce ethanol. Various component and component concentrations in the medium are effective for providing high levels of ethanol productivity. Eliminating certain components and reducing required concentrations levels of other components while maintaining ethanol productivity may provide significant cost savings, especially at a commercial scale fermentation.

The Wood-Ljungdahl pathway is well known in the art and includes reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. Acetyl-CoA may then be converted to ethanol. Enzymes catalyze reactions in the Wood-Ljundahl pathway and those enzyme require various elements for optimal functionality. For example, formate dehydrogenase, an important enzyme in the Wood-Ljungdahl pathway, requires selenium for optimal activity.

SUMMARY

A process for fermenting syngas and a fermentation medium provides high ethanol productivity while removing medium components that were previously thought to be essential. Removal of certain medium components and reducing concentrations of other medium components provides significant operational cost savings at a commercial scale.

A process for reducing selenium levels in cell biomass from fermentation of a CO-containing gaseous substrate includes fermenting the CO-containing gaseous substrate in a fermentation medium. The process is effective for providing a specific STY of at least about 1 gram of ethanol/(L·day·gram cells) and for providing a selenium content in cell biomass exiting the fermentation of about 1 ppm or less.

A process for fermenting a CO-containing gaseous substrate includes fermenting the CO-containing gaseous substrate in a fermentation medium having less than about 1 ppm selenium. The process is effective for providing a specific STY of at least about 1 gram of ethanol/(L·day·gram cells).

A fermentation medium includes at least about 112 mg of nitrogen per gram of cells, at least about 10.5 mg of phosphorous per gram of cells, or at least about 26 mg of potassium per gram of cells. The fermentation medium has less than about 1.04 ppm boron, less than about 0.16 ppm manganese, less than about 0.26 ppm molybdenum, less than about 1 ppm selenium, or less than about 0.16 ppm copper.

BRIEF DESCRIPTION OF THE FIGURES

The above and other aspects, features and other advantages of several aspects of the process will be more apparent from the following figures.

DETAILED DESCRIPTION

The following description is not to be taken in a limiting sense, but is made merely for the purpose of describing the general principles of exemplary aspects. The scope of the invention should be determined with reference to the claims.

A process and medium composition are provided that surprisingly and unexpectedly provides a high level of ethanol productivity even after removing or reducing concentrations of selenium that were previously thought to be essential or required at certain concentration levels.

Syngas fermentations conducted in bioreactors with medium and acetogenic bacteria as described herein are effective for providing conversions of CO in syngas into alcohols and other products. In this aspect, productivity may be expressed as STY (space time yield expressed as g total alcohol/(L·day). In this aspect, the process is effective for providing a STY (space time yield) of at least about 10 g or more total alcohol/(L·day). Possible STY values include about 10 g total alcohol/(L·day) to about 200 g total alcohol/(L·day), in another aspect, about 10 g total alcohol/(L·day) to about 160 g total alcohol/(L·day), in another aspect, about 10 g total alcohol/(L·day) to about 120 g total alcohol/(L·day), in another aspect, about 10 g total alcohol/(L·day) to about 80 g total alcohol/(L·day), in another aspect, about 20 g total alcohol/(L·day) to about 140 g total alcohol/(L·day), in another aspect, about 20 g total alcohol/(L·day) to about 100 g total alcohol/(L·day), in another aspect, about 40 g total alcohol/(L·day) to about 140 g total alcohol/

(L·day), and in another aspect, about 40 g total alcohol/(L·day) to about 100 g total alcohol/(L·day).

Definitions

Unless otherwise defined, the following terms as used throughout this specification for the present disclosure are defined as follows and can include either the singular or plural forms of definitions below defined:

The term "about" modifying any amount refers to the variation in that amount encountered in real world conditions, e.g., in the lab, pilot plant, or production facility. For example, an amount of an ingredient or measurement employed in a mixture or quantity when modified by "about" includes the variation and degree of care typically employed in measuring in an experimental condition in production plant or lab. For example, the amount of a component of a product when modified by "about" includes the variation between batches in a multiple experiments in the plant or lab and the variation inherent in the analytical method. Whether or not modified by "about," the amounts include equivalents to those amounts. Any quantity stated herein and modified by "about" can also be employed in the present disclosure as the amount not modified by "about".

The term "gaseous substrate" is used in a non-limiting sense to include substrates containing or derived from one or more gases.

The term "syngas" or "synthesis gas" means synthesis gas which is the name given to a gas mixture that contains varying amounts of carbon monoxide and hydrogen. Examples of production methods include steam reforming of natural gas or hydrocarbons to produce hydrogen, the gasification of coal and in some types of waste-to-energy gasification facilities. The name comes from their use as intermediates in creating synthetic natural gas (SNG) and for producing ammonia or methanol. Syngas is combustible and is often used as a fuel source or as an intermediate for the production of other chemicals.

The term "fermentor" includes a fermentation device consisting of one or more vessels and/or towers or piping arrangements, which includes the Continuous Stirred Tank Reactor (CSTR), Immobilized Cell Reactor (ICR), Trickle Bed Reactor (TBR), Moving Bed Biofilm Reactor (MBBR), Bubble Column, Gas Lift Fermenter, Membrane Reactor such as Hollow Fibre Membrane Bioreactor (HFMBR), Static Mixer, or other vessel or other device suitable for gas-liquid contact.

The terms "fermentation", fermentation process" or "fermentation reaction" and the like are intended to encompass both the growth phase and product biosynthesis phase of the process. In one aspect, fermentation refers to conversion of CO to alcohol.

The term "cell density" means mass of microorganism cells per unit volume of fermentation broth, for example, grams/liter.

The term "increasing the efficiency", "increased efficiency" and the like, when used in relation to a fermentation process includes increasing one or more of the rate of growth of microorganisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of fermentation.

As used herein, "total alcohol" includes ethanol, butanol, propanol and methanol. In one aspect, the total alcohol may include at least about 75 weight percent or more ethanol, in another aspect, about 80 weight percent or more ethanol, in another aspect, about 85 weight percent or more ethanol, in another aspect, about 90 weight percent or more ethanol, and in another aspect, about 95 weight percent or more ethanol. In another aspect, total alcohol may include about 25 weight percent or less butanol.

The term "specific CO uptake" means an amount of CO in mmoles consumed by unit mass of microorganism cells (g) per unit time in minutes, i.e. mmole/gram/minute.

CO-Containing Substrate

A CO-containing substrate may include any gas that includes CO. In this aspect, a CO-containing gas may include syngas, industrial gases, and mixtures thereof.

Syngas may be provided from any know source. In one aspect, syngas may be sourced from gasification of carbonaceous materials. Gasification involves partial combustion of biomass in a restricted supply of oxygen. The resultant gas mainly includes CO and $H_2$. In this aspect, syngas will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. Some examples of suitable gasification methods and apparatus are provided in U.S. Ser. Nos. 61/516,667, 61/516,704 and 61/516,646, all of which were filed on Apr. 6, 2011, and in U.S. Ser. Nos. 13/427,144, 13/427,193 and 13/427,247, all of which were filed on Mar. 22, 2012, and all of which are incorporated herein by reference.

In another aspect, the process has applicability to supporting the production of alcohol from gaseous substrates such as high volume CO-containing industrial flue gases. In some aspects, a gas that includes CO is derived from carbon containing waste, for example, industrial waste gases or from the gasification of other wastes. As such, the processes represent effective processes for capturing carbon that would otherwise be exhausted into the environment. Examples of industrial flue gases include gases produced during ferrous metal products manufacturing, non-ferrous products manufacturing, petroleum refining processes, gasification of coal, gasification of biomass, electric power production, carbon black production, ammonia production, methanol production and coke manufacturing.

Depending on the composition of the CO-containing substrate, the CO-containing substrate may be provided directly to a fermentation process or may be further modified to include an appropriate $H_2$ to CO molar ratio. In one aspect, CO-containing substrate provided to the fermentor has an $H_2$ to CO molar ratio of about 0.2 or more, in another aspect, about 0.25 or more, and in another aspect, about 0.5 or more. In another aspect, CO-containing substrate provided to the fermentor may include about 40 mole percent or more CO plus $H_2$ and about 30 mole percent or less CO, in another aspect, about 50 mole percent or more CO plus $H_2$ and about 35 mole percent or less CO, and in another aspect, about 80 mole percent or more CO plus $H_2$ and about 20 mole percent or less CO.

In one aspect, the CO-containing substrate mainly includes CO and $H_2$. In this aspect, the CO-containing substrate will contain at least about 10 mole % CO, in one aspect, at least about 20 mole %, in one aspect, about 10 to about 100 mole %, in another aspect, about 20 to about 100 mole % CO, in another aspect, about 30 to about 90 mole % CO, in another aspect, about 40 to about 80 mole % CO, and in another aspect, about 50 to about 70 mole % CO. The CO-containing substrate will have a CO/$CO_2$ ratio of at least about 0.75, in another aspect, at least about 1.0, and in another aspect, at least about 1.5.

In one aspect, a gas separator is configured to substantially separate at least one portion of the gas stream, wherein the portion includes one or more components. For example, the gas separator may separate $CO_2$ from a gas stream comprising the following components: CO, $CO_2$, $H_2$, wherein the $CO_2$ may be passed to a $CO_2$ remover and the remainder of the gas stream (comprising CO and $H_2$) may be passed to a bioreactor. Any gas separator known in the art may be utilized. In this aspect, syngas provided to the fermentor will have about 10 mole % or less $CO_2$, in another aspect, about 1 mole % or less $CO_2$, and in another aspect, about 0.1 mole % or less $CO_2$.

Certain gas streams may include a high concentration of CO and low concentrations of $H_2$. In one aspect, it may be desirable to optimize the composition of the substrate stream in order to achieve higher efficiency of alcohol production and/or overall carbon capture. For example, the concentration of $H_2$ in the substrate stream may be increased before the stream is passed to the bioreactor.

According to particular aspects of the invention, streams from two or more sources can be combined and/or blended to produce a desirable and/or optimized substrate stream. For example, a stream comprising a high concentration of CO, such as the exhaust from a steel mill converter, can be combined with a stream comprising high concentrations of $H_2$, such as the off-gas from a steel mill coke oven.

Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Bioreactor Design and Operation

Descriptions of fermentor designs are described in U.S. Ser. Nos. 13/471,827 and 13/471,858, both filed May 15, 2012, and U.S. Ser. No. 13/473,167, filed May 16, 2012, all of which are incorporated herein by reference.

In accordance with one aspect, the fermentation process is started by addition of medium to the reactor vessel. Some examples of medium compositions are described in U.S. Ser. Nos. 61/650,098 and 61/650,093, filed May 22, 2012, and in U.S. Pat. No. 7,285,402, filed Jul. 23, 2001, all of which are incorporated herein by reference. The medium may be sterilized to remove undesirable microorganisms and the reactor is inoculated with the desired microorganisms. Sterilization may not always be required.

In one aspect, the microorganisms utilized include acetogenic bacteria. Examples of useful acetogenic bacteria include those of the genus *Clostridium*, such as strains of *Clostridium ljungdahlii*, including those described in WO 2000/68407, EP 117309, U.S. Pat. Nos. 5,173,429, 5,593,886 and 6,368,819, WO 1998/00558 and WO 2002/08438, strains of *Clostridium autoethanogenum* (DSM 10061 and DSM 19630 of DSMZ, Germany) including those described in WO 2007/117157 and WO 2009/151342 and *Clostridium ragsdalei* (P11, ATCC BAA-622) and *Alkalibaculum bacchi* (CP11, ATCC BAA-1772) including those described respectively in U.S. Pat. No. 7,704,723 and "Biofuels and Bioproducts from Biomass-Generated Synthesis Gas", Hasan Atiyeh, presented in Oklahoma EPSCoR Annual State Conference, Apr. 29, 2010 and *Clostridium carboxidivorans* (ATCC PTA-7827) described in U.S. Patent Application No. 2007/0276447. Other suitable microorganisms includes those of the genus *Moorella*, including *Moorella* sp. HUC22-1, and those of the genus *Carboxydothermus*. Each of these references is incorporated herein by reference. Mixed cultures of two or more microorganisms may be used.

Some examples of useful bacteria include *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter subterraneous pacificus, Carboxydothermus hydrogenoformans, Clostridium aceticum, Clostridium acetobutylicum, Clostridium acetobutylicum* P262 (DSM 19630 of DSMZ Germany), *Clostridium autoethanogenum* (DSM 19630 of DSMZ Germany), *Clostridium autoethanogenum* (DSM 10061 of DSMZ Germany), *Clostridium autoethanogenum* (DSM 23693 of DSMZ Germany), *Clostridium autoethanogenum* (DSM 24138 of DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 of DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, Geobacter sulfurreducens, Methanosarcina acetivorans, Methanosarcina barkeri, Morrella thermoacetica, Morrella thermoautotrophica, Oxobacter pfennigii, Peptostreptococcus productus, Ruminococcus productus, Thermoanaerobacter kivui*, and mixtures thereof.

All strains of this group have a genome size of around 4.2 MBp (Kopke et al., 2010) and a GC composition of around 32% mol (Abrini et al., 1994; Kopke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde:ferredoxin oxidoreductase (Kopke et al., 2010, 2011). The organization and number of Wood-Ljungdahl pathway genes, responsible for gas uptake, has been found to be the same in all species, despite differences in nucleic and amino acid sequences (Kopke et al., 2011).

The strains all have a similar morphology and size (logarithmic growing cells are between 0.5-0.7×3-5 μm), are mesophilic (optimal growth temperature between 30-37° C.) and strictly anaerobe (Abrini et al., 1994; Tanner et al., 1993)(WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Kopke et al., 2011; Tanner et al., 1993)(WO 2008/028055). Indole production has been observed with all species. However, the species differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not.

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The methods of the invention can be used to sustain the viability of a microbial culture, wherein the microbial culture is limited in CO, such that the rate of transfer of CO into solution is less than the uptake rate of the culture. Such situations may arise when a substrate comprising CO is not continuously provided to the microbial culture; the mass transfer rate is low; or there is insufficient CO in a substrate stream to sustain culture vitality at optimum temperature. In such embodiments, the microbial culture will rapidly deplete the CO dissolved in the liquid nutrient medium and become substrate limited as further substrate cannot be provided fast enough.

Startup:

Upon inoculation, an initial feed gas supply rate is established effective for supplying the initial population of microorganisms. Effluent gas is analyzed to determine the content of the effluent gas. Results of gas analysis are used to control feed gas rates. In this aspect, the process provides a calculated CO concentration to initial cell density ratio of about 0.5 to about 0.9, in another aspect, about 0.6 to about 0.8, in another aspect, about 0.5 to about 0.7, and in another aspect, about 0.5 to about 0.6.

In another aspect, a fermentation process includes providing syngas to a fermentation medium in an amount effective for providing an initial calculated CO concentration in the fermentation medium of about 0.15 mM to about 0.70 mM, in another aspect, about 0.15 mM to about 0.50 mM, in another aspect, about 0.15 mM to about 0.35 mM, in another aspect, about 0.20 mM to about 0.30 mM, and in another aspect, about 0.23 mM to about 0.27 mM. The process is effective for increasing cell density as compared to a starting cell density.

Post-Startup:

Upon reaching desired levels, liquid phase and cellular material is withdrawn from the reactor and replenished with medium. The process is effective for increasing cell density to about 2.0 grams/liter or more, in another aspect, about 2 to about 30 grams/liter, in another aspect, about 2 to about 25 grams/liter, in another aspect, about 2 to about 20 grams/liter, in another aspect, about 2 to about 10 grams/liter, in another aspect, about 2 to about 8 grams/liter, in another aspect, about 3 to about 30 grams/liter, in another aspect, about 3 to about 6 grams/liter, and in another aspect, about 4 to about 5 grams/liter.

Medium Composition

In one aspect, the medium includes at least one or more of a nitrogen source, at least one or more phosphorous source and at least one or more of a potassium source. The medium may include any one of the three, any combination of the three, and in an important aspect, includes all three. A nitrogen source may include a nitrogen source selected from the group consisting of ammonium chloride, ammonium hydroxide, ammonium phosphate, ammonium sulfate, ammonium nitrate, and mixtures thereof. A phosphorous source may include a phosphorous source selected from the group consisting of phosphoric acid, ammonium phosphate, potassium phosphate, and mixtures thereof. A potassium source may include a potassium source selected from the group consisting of potassium chloride, potassium phosphate, potassium nitrate, potassium sulfate, and mixtures thereof.

In one aspect, the medium includes one or more of iron, tungsten, nickel, cobalt, magnesium, sulfur and thiamine. The medium may include any one of these components, any combination, and in an important aspect, includes all of these components. An iron may include an iron source selected from the group consisting of ferrous chloride, ferrous sulfate, and mixtures thereof. A tungsten source may include a tungsten source selected from the group consisting of sodium tungstate, calcium tungstate, potassium tungstate, and mixtures thereof. A nickel source may include a nickel source selected from the group consisting of nickel chloride, nickel sulfate, nickel nitrate, and mixtures thereof. A cobalt source may include a cobalt source selected from the group consisting of cobalt chloride, cobalt fluoride, cobalt bromide, cobalt iodide and mixtures thereof. A magnesium source may include a magnesium source selected from the group consisting of magnesium chloride, magnesium sulfate, magnesium phosphate, and mixtures thereof. A sulfur source may include cysteine, sodium sulfide, and mixtures thereof.

Concentrations of various components are as follows:

| Component | Concentration Range (expressed as mg or µg nutrient per gram of cells) | Preferred Range (expressed as mg or µg nutrient per gram of cells) |
| --- | --- | --- |
| nitrogen (N) | 112-160 mg | 140-150 mg |
| phosphorus (P) | 10.5-15 mg | 12-13 mg |
| potassium (K) | 26-36 mg | 28-33 mg |
| iron (Fe) | 2.7-5 mg | 3.0-4.0 mg |
| tungsten (W) | 10-30 µg | 15-25 µg |
| Nickel (Ni) | 34-40 µg | 35-37 µg |
| Cobalt (Co) | 9-30 µg | 15-20 µg |
| Magnesium (Mg) | 4.5-10 mg | 5-7 mg |
| Sulfur (S) | 11-20 mg | 12-16 mg |
| Thiamine | 6.5-20 µg | 7-12 µg |

Process operation maintains a pH in a range of about 4.2 to about 4.8. The medium includes less than about 0.01 g/L yeast extract and less than about 0.01 g/L carbohydrates.

In this aspect, the medium may have reduced concentration levels of one or more nutrients that include B, Mn, Mo and Cu. Nutrient concentrations in the medium may be as follows:

B: less than about 1.04 ppm B, in another aspect, less than about 1.0 ppm B, in another aspect, less than about 0.75 ppm B, in another aspect, less than about 0.5 ppm B, and in another aspect, less than about 0.025 ppm B;

Mn: less than about 0.16 ppm Mn, in another aspect, less than about 0.15 ppm Mn, in another aspect, less than about 0.10 ppm Mn, in another aspect, less than about 0.05 ppm Mn, and in another aspect, less than about 0.0025 ppm Mn;

Mo: less than about 0.26 ppm Mo, in another aspect, less than about 0.25 ppm Mo, in another aspect, less than about 0.20 ppm Mo, in another aspect, less than about 0.10 ppm Mo, and in another aspect, less than about 0.001 ppm Mo; or Cu: less than about 0.16 ppm Cu, in another aspect, less than about 0.15 ppm Cu, in another aspect, less than about 0.10 ppm B, in another aspect, less than about 0.05 ppm B, and in another aspect, less than about 0.01 ppm B.

In another aspect, weight ratios may be as follows:

$NH_4^+$ to B: about 625:1 or more, in another aspect, about 650:1 or more, in another aspect, about 675:1 or more, in another aspect, about 700:1 or more, in another aspect, about 750:1 or more, and in another aspect, about 800:1 or more; or $NH_4^+$ to Mn: about 4050:1 or more, in another aspect, about 4100:1 or more, in another aspect, about 4200:1 or more, in another aspect, about 4300:1 or more, in another aspect, about 4400:1 or more, and in another aspect, about 4500:1 or more; or $NH_4^+$ to Mo: about 2500:1 or more, in another aspect, about 2600:1 or more, in another aspect, about 2700:1 or more, in another aspect, about 2800:1 or more, in another aspect, about 2900:1 or more, and in another aspect, about 3000:1 or more; or $NH_4^+$ to Cu: about 4050:1 or more; in another aspect, about 4100:1 or more, in another aspect, about 4200:1 or more, in another aspect, about 4300:1 or more, in another aspect, about 4400:1 or more, and in another aspect, about 4500:1 or more; or P to B: about 30:1 or more, in another aspect, about 35:1 or more, in another aspect, about 40:1 or more, in another aspect, about 45:1 or more, in another aspect, about 50:1 or more, and in another aspect, about 100:1 or more; or P to Mn: about 190:1 or more, in another aspect, about 200:1 or more, in another aspect, about 225:1 or more, in another aspect, about 250:1 or more, in another aspect, about 275:1 or more, and in another aspect, about 300:1 or more; or P to Mo: about 120:1 or more, in another aspect, about 130:1 or more, in another aspect, about 140:1 or more, in another aspect, about 150:1 or more, in another aspect, about 175:1 or more, and in another aspect, about 200:1 or more; or P to Cu: about 190:1 or more; in another aspect, about 200:1 or more, in another aspect, about 225:1 or more, in another aspect, about 250:1 or more, in another aspect, about 275:1 or more, and in another aspect, about 300:1 or more; or K to B: about 35:1 or more, in another aspect, about 40:1 or more, in another aspect, about 45:1 or more, in another aspect, about 50:1 or more, in another aspect, about 75:1 or more, and in another aspect, about 100:1 or more; or K to Mn: about 245:1 or more, in another aspect, about 250:1 or more, in another aspect, about 260:1 or more, in another aspect, about 270:1 or more, in another aspect, about 280:1 or more, and in another aspect, about 300:1 or more; or K to Mo: about 150:1 or more, in another aspect, about 250:1 or more, in another aspect, about 260:1 or more, in another aspect, about 270:1 or more, in another aspect, about 280:1 or more, and in another aspect, about 300:1 or more; or K to Cu: about 245:1 or more, in another aspect, about 250:1 or more, in another aspect, about 260:1 or more, in another aspect, about 270:1 or more, in another aspect, about 280:1 or more, and in another aspect, about 300:1 or more.

In another aspect, the process and media are effective for providing a CO conversion of at least about 5% to about 99%, in another aspect, about 10% to about 90%, in another aspect, about 20% to about 80%, in another aspect, about 30% to about 70%, and in another aspect, about 40% to about 90%.

In another aspect, the process and media are effective for providing a Se level in biomass exiting the fermentation of about 1 ppm or less. In another aspect, about 0.75 ppm or less, and in another aspect, about 0.5 ppm or less, all on a dry weight basis. In another aspect, the Se level in biomass exiting the fermentation may be about 0.01 to about 1 ppm, in another aspect, about 0.01 to about 0.9 ppm, in another aspect, about 0.01 to about 0.75 ppm, in another aspect, about 0.01 to about 0.5 ppm, in another aspect, about 0.01 to about 0.25 ppm, in another aspect, about 0.025 to about 1 ppm, in another aspect, about 0.025 to about 0.9 ppm, in another aspect, about 0.025 to about 0.75 ppm, in another aspect, about 0.025 to about 0.5 ppm, in another aspect, about 0.5 to about 1 ppm, in another aspect, about 0.5 to about 0.9 ppm, and in another aspect, about 0.5 to about 0.75 ppm. In one aspect, Se may include other forms of selenium including −2, +2, +4 and +6 oxidation states, and may include for example, selenite and selenate. The indicates ranges refer to Se equivalents.

EXAMPLES

Example 1

Evaluation of Culture Growth in Medium with Sodium Selenite

Preparation of Medium:
Medium was prepared as follows:

|  | Amount |
|---|---|
| 1x Medium | |
| $FeCl_2 \cdot 4H_2O$ (g) | 0.24 |
| $H_3PO_4$ (85%) (mL) | 0.86 |
| KCl (g) | 3.00 |
| $MgCl_2 \cdot 6H2O$ (g) | 0.48 |
| Water (L) | 9.50 |
| 6x Med A2 (mL) | 15.0 |
| 6x TE (mL) | 4.6 |
| Vitamins* (mL) | 8.3 |
| Water (L) | To 10 L |
| 6x Medium A2 | |
| $Na_2SeO_3$ (g) | 0.08 |
| $Na_2WO_4 \cdot 2H_2O$ (g) | 1.92 |
| $H_3PO_4$ (85%) (mL) | 0.00 |
| Water (mL) | to 500 |
| 6x TE | |
| $H_3PO_4$ (85%) (mL) | 68.2 |
| $CoCl_2 \cdot 6H_2O$ (g) | 0.88 |
| $NiCl_2 \cdot 6H_2O$ (g) | 0.00 |
| $ZnSO_4 \cdot 7H_2O$ (g) | 1.07 |
| Water (mL) | to 500 |

*Vitamin Solution: Biotin, 0.04 g/L; Thiamine HCl, 0.1 g/L and Calcium d-Pantothenate, 0.0505 g/L Reactor Inoculation and Maintenance:

A BioFlo 310 series reactor (New Brunswick) was setup for anaerobic fermentation to include gas lines, both in and out, culture purge, feed lines, and a cell recycle system including permeate draw. Before inoculation, the reactor was filled with 2 L of medium and purged with syngas for at least 2 hours, temperature was raised to 38° C. and pH was brought to and maintained between 4.4 and 4.7 using 0.5M $NH_4OH$. Sodium hydrosulfide (0.2% v/v) was mixed with the reactor medium to a final concentration of $9 \times 10^{-4}$% v/v. For the duration of the experiment, agitation was kept at 800 rpm.

The reactor was inoculated with exponentially growing cells from a parent reactor to achieve an initial cell concentration of 0.3 g/L (Dry cell weight). Starting with a gas flow rate of 15 mL/min of syngas (30% CO, 15% $H_2$, 10% $CO_2$), 10% gas flow increases were performed on an hourly bases to support cell growth and maintain $H_2$ and CO conversions >25% and >80%, respectively as determined by gas chromatography (GC, SR18610C). Throughout the experiment, the gas flow rate was maintained between 250-300 mL/min. Medium flow was adjusted to achieve 18-24 hr liquid retention time and cell density was controlled using a hollow fiber-based cell recycle system. Sodium hydrosulfide (0.2% v/v) was continuously mixed directly with the reactor medium at a constant rate of 0.2 mL/min. Once the culture reached a cell density of 2.5 to 3 g/L of dry cell weight (determined by $OD_{580}$), the cell recycle system was turn off and the reactor was run as a once through system. To analyze product formation, liquid samples were taken every 4 hours and analyzed using a Liquid GC, Shimadzu GC-2014. Reactors were maintained at steady state for at least 5 days.

Figure 1:
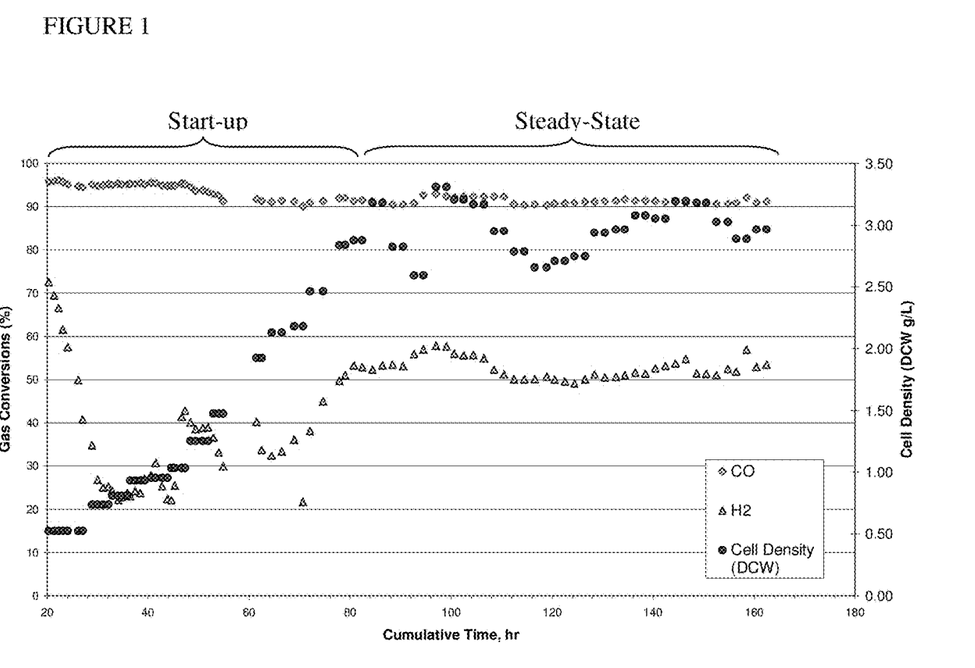
FIG. 1 illustrates gas conversions and cell density from inoculation of *Clostridium ljungdahlii* C-01 in medium containing no Selenium.

The following table summarizes steady state fermentation performance in medium containing selenium (Se(+)) and FIG. 1 illustrates cell growth and gas conversions over time.

| Medium | | |
|---|---|---|
| | Se (+) | |
| | Average | SD |
| Cell Density (g/L) | 2.96 | 0.21 |
| Cell Retention Time (hrs) | 22.78 | 2.93 |
| EtOH (g/L) | 12.49 | 0.63 |
| HAc (g/L) | 3.19 | 0.6 |
| BuOH (g/L) | 0.22 | 0.02 |
| $H_2$ Conversions (%) | 52.68 | 0.25 |
| CO Conversions (%) | 91.36 | 0.73 |
| EtOH Productivity (g/L/day) | 13.4 | 2.04 |
| Specific EtOH Productivity (g/L/day/g dry cells) | 4.55 | 0.75 |
| HAc Productivity (g/L/day) | 3.72 | 0.5 |
| Specific Hac Productivity (g/L/day/g cells) | 1.32 | 0.18 |
| EtOH/Acetate ratio | 4.05 | 0.74 |
| EtOH/BuOH ratio | 57.88 | 5.79 |
| Total Productivity (g/L/day) | 16.78 | 2.15 |

Example 2

Evaluation of Culture Growth in Medium without Sodium Selenite

Preparation of Medium:

The Selenium (−) medium was prepared as in Example 1 except that sodium selenite was omitted from the recipe.

Reactor Inoculation and Maintenance:

A setup was used as described in Example 1.

Figure 2:
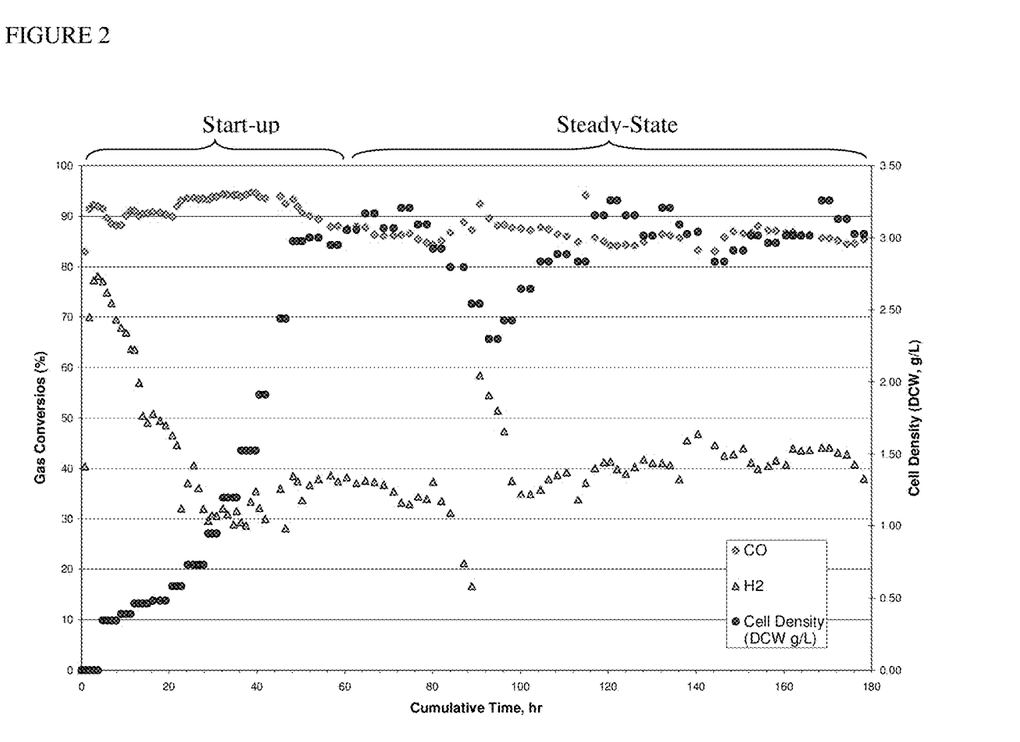
FIG. 2 illustrates gas conversions and cell density from inoculation of *Clostridium ljungdahlii* C-01 in medium containing Selenium.

The following table summarizes fermentation performance in medium without selenium (Se (−)) and FIG. 2 illustrates cell growth and gas conversions over time.

| Medium | | |
|---|---|---|
| | Se (−) | |
| | Average | SD |
| Cell Density (g/L) | 2.96 | 0.2 |
| Cell Retention Time (hrs) | 25.65 | 1.91 |
| EtOH (g/L) | 13.67 | 0.97 |
| HAc (g/L) | 2.38 | 0.4 |
| BuOH (g/L) | 0.21 | 0.02 |
| $H_2$ Conversions (%) | 42.02 | 5.59 |
| CO Conversions (%) | 85.03 | 2.27 |
| EtOH Productivity (g/L/day) | 12.88 | 1.53 |
| Specific EtOH Productivity (g/L/day/g dry cells) | 4.36 | 0.48 |
| HAc Productivity (g/L/day) | 2.24 | 0.38 |
| Specific Hac Productivity (g/L/day/g cells) | 0.76 | 0.15 |
| EtOH/Acetate ratio | 5.93 | 1.23 |
| EtOH/BuOH ratio | 67.35 | 8.24 |
| Total Productivity (g/L/day) | 15.06 | 1.61 |

Example 3

Quantitation of Se in the Cell Mass

At the time of reactor shutdown, 200 mL of culture was removed and centrifuged at 4,000 rpm for 5 min at 4° C. in an Allegra 25R centrifuge (Beckman Coulter). The pellet was then washed and resuspended with ice cold 50 mL of 0.8% NaCl solution and once again centrifuged. The resulting pellet was stored at −80° C. until processing. In parallel, medium samples were analyzed for the presence of Se using standard inductively couple plasma analysis (ICP) method as described in 'Standard Methods for the Examination of Water and Wastewater" $19^{th}$ edition, A. D. Eaton, L. S. Clesceri and A. E. Greenberg, 1995, pp 3-34 Chapter 3120 B.

Cell Analysis:

Selenium content of the cells was determined using inductively couple plasma analysis (ICP) analysis. Samples were initially digested with nitric acid (5% v/v) and $H_2O_2$ (10% v/v) at 120° C. for 2 hours to dissolve the cells ('Standard Methods for the Examination of Water and Wastewater" $19^{th}$ edition, A. D. Eaton, L. S. Clesceri and A. E. Greenberg, 1995, pp 3-5, Chapter 3030 E) and the resulting digest was subjected to ICP.

Results:

Evaluation of selenium content in media. The table below summarizes the metal content in Se (+) and Se-free medium used in the experiment. Note that the Se content in the Se-free medium is at the limit of detection using standard ICP analysis is i.e. 0.03 ppm (*)

| | Medium Se (+) | | Medium Se (−) | |
|---|---|---|---|---|
| Elements | Concentrations (ppm) | SD (ppm) | Concentrations (ppm) | SD (ppm) |
| Cl | 114.2 | 3.83 | 112.3 | 3.21 |
| Co | 0.1981 | 0.004 | 0.1995 | 0.001 |
| Fe | 6.784 | 0.12 | 6.770 | 0.07 |
| K | 270.3 | 2.45 | 261.6 | 3.58 |
| Mg | 5.209 | 0.07 | 5.147 | 0.03 |
| Na | 0.8271 | 0.006 | 0.7483 | 0.007 |
| Ni | 0.2408 | 0.003 | 0.2407 | 0.003 |
| P | 69.43 | 1.46 | 66.83 | 0.62 |

-continued

| Elements | Medium Se (+) | | Medium Se (−) | |
| --- | --- | --- | --- | --- |
| | Concentrations (ppm) | SD (ppm) | Concentrations (ppm) | SD (ppm) |
| S | 2.054 | 0.02 | 2.050 | 0.007 |
| Se* | 0.1421 | 0.004 | 0.0322 | 0.000 |
| W | 3.362 | 0.03 | 3.246 | 0.07 |
| Zn | 0.4542 | 0.01 | 0.4502 | 0.005 |

Results:

Evaluation of selenium content in cells. Analysis of Se in cells shows that cells grown in the absence of sodium selenite have a Se content of 484 ppb (~0.5 ppm) compared to 34 ppm in cells grown in the presence of selenium salt. This constitutes a 98.5% reduction in the Se content of the cells.

Example 4

Evaluation of C. autoethanogenum Cell Growth Rate in Se-Free Medium Using Culture Tubes The following medium (1% MES) was utilized for growth in culture tubes.

| | Amount per liter | |
| --- | --- | --- |
| Component | (−) Se | (+) Se |
| MES ($C_6H_{13}NO_4S$) | 10 g | 10 g |
| Mineral Salt Solution[1] | 12.5 mL | 12.5 mL |
| Resazurin solution[2] | 1 mL | 1 mL |
| 85% $H_3PO_4$ | 37.5 mL | 37.5 mL |
| $ZnSO_4 \cdot 7H_2O$ | 0.10 g | 0.10 g |
| $MnCl_2 \cdot 4H_2O$ | 0.03 g | 0.03 g |
| $H_3BO_3$ | 0.30 g | 0.30 g |
| $CoCl_2 \cdot 6H_2O$ | 0.30 g | 0.30 g |
| $CuCl_2 \cdot H_2O$ | 0.02 g | 0.02 g |
| $NiCl_2 \cdot 6H_2O$ | 0.071 g | 0.071 g |
| $NaMoO_4 \cdot 2H_2O$ | 0.03 g | 0.03 g |
| $FeCl_2 \cdot H_2O$ | 2.00 g | 2.00 g |
| $Na_2SeO_3$ | — | 0.01 g |
| $Na_2WO_4 \cdot 2H_2O$ | 0.15 g | 0.15 g |
| Total (in $H_2O$) | 1000 mL | 1000 mL |

[1]Mineral Salt Stock Solution (NaCl 80, g/L; $NH_4Cl$, 100 g/L; KCl, 10 g/L; $KH_2PO_4$, 10 g/L; $MgSO_4 \cdot 7H_2O$, 20 g/L; $CaCl_2 \cdot H_2O$, 4 g/L).
[2]Resazurin solution (1 g/L resazurin sodium salt).

Figure 3:
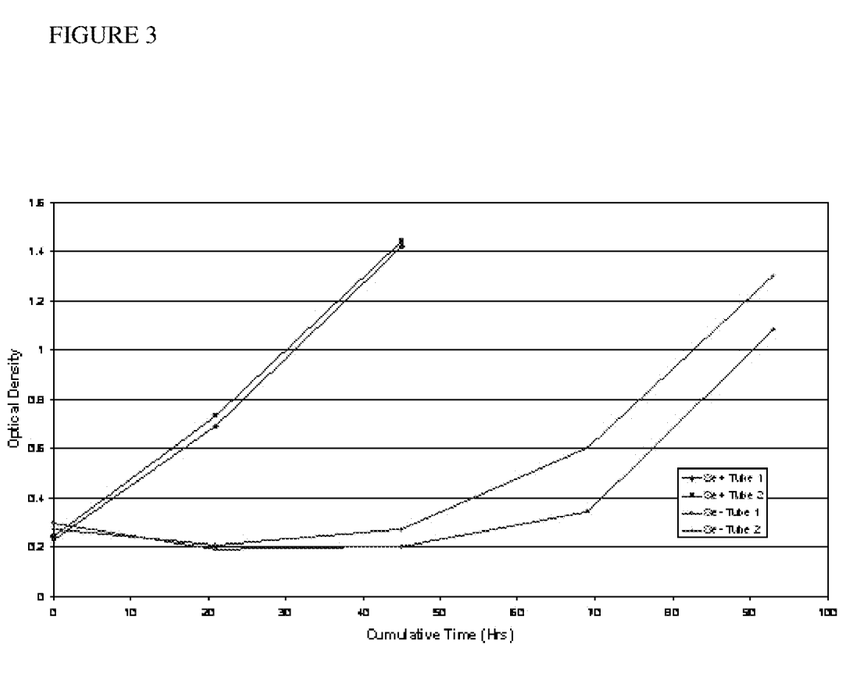
FIG. 3 shows a comparison of growth curves between *C. autoethanogenum* cultures grown in culture tubes with medium with and without selenium.

Culture tubes filled with 4 mL of appropriate medium were inoculated with a frozen stock of C. autoethanogenum (DSM #10061) and pressurized with syngas to 4 psig. To prepare seed cultures, the tubes were gassed daily with syngas until the culture reached an $OD_{580}$ of 1.2. Four ml of 1% MES+Se and/or 1% MES-Se were inoculated with live cells and pressurized with syngas. The inoculum was first centrifuged at 3,000 rpm to pellet the cells in anaerobic conditions. The pellet was subsequently resuspended in fresh Se(+) or Se(−) medium and used to inoculated new culture tubes at a target of $OD_{580}$=0.3. The cultures were then allowed to grow in a 37° C. shaking incubator at 70 rpm. Cultures tubes inoculated with C. autoethanogenum at an initial $OD_{580}$=0.3 in Se (+) or Se(−) 1% MES medium were monitored over time. The optical density of each tube was measured immediately after inoculation and once a day after that. As seen in FIG. 3, cells in both media grew to an $OD_{580}$>1. During the exponential phase both media supported the same growth rate.

Example 5

Evaluation of Fermentation Performance and Productivity of C. autoethanogenum with Se-Free Medium in a Bioreactor C. autoethanogenum culture was used to inoculate a seed reactor containing laboratory medium (1 L reactor, SR07000DLS stirred tank Bioreactor, DASGIP). Inoculation and reactor maintenance was essentially as described in Example 1. Once this culture reached steady state, it was used to inoculate a second reactor containing laboratory medium with no selenium. The daughter culture was then allowed to reach steady-state and was maintained at that state for no less than 72 hours. The parent reactor was also monitored during this time as a comparison.

The following table summarizes the composition of the medium for experiments with C. autoethanogenum.

| | Amount |
| --- | --- |
| 1x Medium (10 L) | |
| $FeCl_2 \cdot 4H_2O$ (g) | 0.30 |
| $H_3PO_4$ (85%) (mL) | 0.75 |
| KCl (g) | 1.50 |
| $MgCl_2 \cdot 6H2O$ (g) | 1.25 |
| Water (L) | 9.50 |
| MPFN (mL) | 75.00 |
| Vitamins* (mL) | 5.00 |
| Water (L) | To 10 L |
| MPFN in 1 L | |
| $Na_2SeO_3$ (g) | 0.02 |
| $Na_2WO_4 \cdot 2H_2O$ (g) | 0.40 |
| $H_3PO_4$ (85%) (mL) | 100 |
| $ZnSO_4 \cdot 7H_2O$ (g) | 0.20 |
| $NiCl_2 \cdot 6H_2O$ (g) | 0.19 |
| $CoCl_2 \cdot 6H_2O$ (g) | 0.80 |
| Water (mL) | to 1000 |

*Vitamin Solution: Biotin, 0.04 g/L; Thiamine HCl, 0.1 g/L and Calcium d-Pantothenate, 0.0505 g/L
Note:
A separate MPFN was prepared with no $Na_2SeO_3$ for the portion of the experiment in which culture was propagated in medium containing no selenium.

The table below summarizes the steady state fermentation performance of C. autoethanogenum in Se(+) and Se(−) media. Parameters in both cases fell within the expected range of performance and showed no significant differences between the two.

| | Se (+) Medium | | Se (−) Medium | |
| --- | --- | --- | --- | --- |
| | Average | SD | Average | SD |
| Cell Density (g/L) | 2.65 | 0.05 | 2.72 | 0.11 |
| Cell Retention Time (hrs) | 22.97 | 0.41 | 21.98 | 1.62 |
| EtOH (g/L) | 15.84 | 0.97 | 13.95 | 0.59 |
| HAc (g/L) | 2.60 | 0.20 | 2.22 | 0.35 |
| BuOH (g/L) | 0.10 | 0.01 | 0.13 | 0.02 |
| $H_2$ Conversions (%) | 46.93 | 1.50 | 41.53 | 1.98 |
| CO Conversions (%) | 88.13 | 0.90 | 87.37 | 1.26 |

Similar trends can be observed in the productivity of each culture as shown below.

|  | Se (+) Medium | | Se (−) Medium | |
| --- | --- | --- | --- | --- |
|  | Average | SD | Average | SD |
| EtOH Productivity (g/L/day) | 16.56 | 1.11 | 15.31 | 1.19 |
| Specific EtOH Productivity (g/L/day/g cells) | 6.24 | 0.39 | 5.63 | 0.58 |
| HAc Productivity (g/L/day) | 2.72 | 0.22 | 2.44 | 0.43 |
| Specific Hac Productivity (g/L/day/g cells) | 1.03 | 0.08 | 0.90 | 0.17 |
| EtOH/Acetate ratio | 6.13 | 0.68 | 6.49 | 1.37 |
| EtOH/BuOH ratio | 154.04 | 14.92 | 108.50 | 11.58 |
| Total Productivity (g/L/day) | 19.28 | 1.08 | 17.74 | 1.30 |

While the invention herein disclosed has been described by means of specific aspects, examples and applications thereof, numerous modifications and variations could be made thereto by those skilled in the art without departing from the scope of the invention set forth in the claims.

What is claimed is:

1. A process for reducing selenium levels in cell biomass from fermentation of a CO-containing gaseous substrate, the method comprising:

providing a fermentation medium to a bioreactor, the fermentation medium comprising about 112 to about 160 mg of nitrogen per gram of cells, about 10.5 to about 15 mg of phosphorous per gram of cells, about 26 to about 36 mg of potassium per gram of cells, less than about 0.01 g/L yeast extract, and less than about 0.01 g/L carbohydrates;

providing the CO-containing gaseous substrate to the bioreactor, the CO-containing gaseous substrate comprising at least about 10 mole % CO and having a CO/CO2 ratio of at least about 0.75;

fermenting the CO-containing gaseous substrate in a fermentation medium with acetogenic bacteria selected from the group consisting of *Clostridium autoethanogenum* (DSM 10061 of DSMZ Germany), *Clostridium coskatii* (ATCC PTA-10522), *Clostridium ljungdahlii* PETC (ATCC 49587), *Clostridium ljungdahlii* ER12 (ATCC 55380), *Clostridium ljungdahlii* C-01 (ATCC 55988), *Clostridium ljungdahlii* O-52 (ATCC 55889), and mixtures thereof;

wherein the fermentation medium has less than 1 ppm selenium, wherein the selenium is in the form of selenite or selenate, wherein the process provides a specific STY of at, least about 1 gram of ethanol/(L·day·gram cells), and wherein the process provides a selenium content in cell biomass exiting the fermentation of about 1 ppm or less.

2. The fermentation process of claim 1 wherein a pH of the fermentation medium is maintained in a range of about 4.2 to about 4.8.

* * * * *